United States Patent [19]

Regunathan et al.

[11] Patent Number: 5,574,059
[45] Date of Patent: Nov. 12, 1996

[54] TREATING DISORDERS MEDIATED BY VASCULAR SMOOTH MUSCLE CELL PROLIFERATION

[75] Inventors: Soundararajan Regunathan, Avenel, N.J.; Donald J. Reis, New York, N.Y.

[73] Assignee: Cornell Research Foundation, Inc., Ithaca, N.Y.

[21] Appl. No.: 548,973

[22] Filed: Oct. 27, 1995

[51] Int. Cl.$^6$ .................................................. A61K 31/415
[52] U.S. Cl. ............................................................ 514/397
[58] Field of Search ............................................. 514/397

[56] References Cited

U.S. PATENT DOCUMENTS

| | | | |
|---|---|---|---|
| 4,507,321 | 3/1985 | Raisfeld | 514/673 |
| 4,818,764 | 4/1989 | Chapleo et al. | 514/397 |
| 5,059,624 | 10/1991 | Monache et al. | 514/616 |
| 5,344,846 | 9/1994 | Jakus et al. | 514/634 |

FOREIGN PATENT DOCUMENTS 2068376   8/1981   United Kingdom.

OTHER PUBLICATIONS

Jackson, C. L., et al, Hypertension 20, 713–716 (1992).
Nakaki, T., et al, Molecular Pharmacology 37, 30–36 (1989).
Regunathan, S., et al, Annals of the New York Academy of Sciences, vol. 763, 580–590 (Jul. 1995).

*Primary Examiner*—Raymond Henley, III

[57] ABSTRACT

Disorders mediated by vascular smooth muscle proliferation are treated by administering a vascular smooth muscle antiproliferative effective amount of an $I_2$ imidazoline receptor agonist. The disorders include atherosclerosis, risk of blockage of artery after coronary angioplasty or blood vessel injury from non-angioplasty cause, and proliferative diabetic retinopathy. $I_2$ imidazoline receptor agonists include idazoxan, UK 14,304, naphazoline, cirazoline and agmatine.

8 Claims, No Drawings

TREATING DISORDERS MEDIATED BY VASCULAR SMOOTH MUSCLE CELL PROLIFERATION

This invention was made at least in part with Government support under National Institutes of Health grant number HL 18974. The Government has certain rights in the invention.

TECHNICAL FIELD

This invention is directed to treating patients having pathological conditions, or at risk for such, involving proliferation of vascular smooth muscle cells.

BACKGROUND OF THE INVENTION

A major pathogenic mechanism contributing to vascular pathology in atherosclerosis, hypertension resulting from renal artery stenosis and other causes, restenosis of coronary and other arteries after coronary angioplasty, insertion of vascular stents or due to non-angioplasty injury to blood vessels and proliferative diabetic retinopathy, is vascular hyperplasia, i.e., the excessive proliferation and hypertrophy of vascular smooth muscle cells. Vascular hyperplasia leads to thickening of the arterial wall, narrowing of the vascular lumen and, ultimately, interruption of organ blood flow and tissue death. Currently, treatments are invasive or are directed at complications. Treatments with agents which are non-toxic and non-invasive to inhibit the initiation and/or progression of vascular hyperplasia would be of great benefit.

SUMMARY OF THE INVENTION

The invention herein is directed at a non-invasive method of inhibiting the initiation or progression of vascular hyperplasia and particularly is directed at a method of inhibiting the proliferation of vascular smooth muscle cells in a patient in need of such inhibiting, said method comprising administering to the patient a vascular smooth muscle cell antiproliferative effective amount of an $I_2$ imidazoline receptor agonist.

Imidazoline receptors are nonadrenergic binding sites for agents such as clonidine and idazoxan which also bind to $\alpha_2$-adrenergic receptors. They are described in the following articles: Brica, G., et al, Eur. J. Pharmacol. 162, 1–9 (1989); Coupry, I., et al, J. Pharmacol. Exp. Ther. 252, 293–299 (1989); Ernsberger, P.R., et al, Eur. J. Pharmacol. 134, 1–(1987); and Wikberg, J.E.S., et al, J. Neurochem. 55, 192–203 (1990). There are at least two major classes of imidazoline receptors, namely $I_1$ imidazoline receptors and $I_2$ imidazoline receptors. The $I_1$ imidazoline receptors bind clonidine, p-aminoclonidine (PAC) and idazoxan with comparable affinities and are believed to be expressed on the cell surface and to mediate the central antihypertensive actions of clonidine, rilmenidine and moxonidine (Ernsberger, P., et al, J. Pharmacol. Exp. Ther. 253, 408–418 (1990); Gomez et al, Eur. J. Pharmacol. 195, 181–191 (1991); Ernsberger, P., et al, J. Pharmacol. Exp. Ther. 264, 172–182 (1993)) and regulate the transcription of biosynthetic enzymes in adrenal chromaffin cells. In contrast, the $I_2$ imidazoline receptors bind idazoxan preferentially over clonidine and p-aminoclonidine and are localized to mitochondrial cells (see Regunathan, S., et al, Biochem. Pharmacol. 45, 1667–1675, 1993; and Tesson, F., et al, Eur. J. Pharmacol. 208, 81–83, 1991) and are widely distributed. It has been speculated that the $I_2$ imidazoline receptors influence renal ion transport, secretion of catecholamines from adrenal chromaffin cells and release of insulin from $\beta$-cells.

The term "$I_2$ imidazoline receptor agonist" is used herein to mean compounds which bind to the $I_2$ imidazoline receptor, and have an inhibition constant $K_i$ in respect to inhibiting binding of $^3$H-idazoxan (5 nM) to rat aortic smooth muscle cells of less than 500 nM and inhibit serum-stimulated proliferation of rat aortic smooth muscle cells but do not antagonize the antiproliferative effect of idazoxan (i.e., shift the concentration/response curve for idazoxan to the right and increase the $IC_{50}$ inhibition of serum-stimulated incorporation of $^3$H-thymidine (as described hereinafter) for idazoxan).

Binding to $I_2$ imidazoline receptors is determined by the following assay. Membranes are prepared from cultured cells for ligand binding as described in Regunathan, S., et al, Biochem. Pharmacol. 45, 1667–1675 (1993) and Regunathan, S., et al, J. Neurosci. Res. 34, 681–688 (1993) and the disclosure in these on this is incorporated herein by reference. In particular, harvested rat aortic smooth muscle cells are homogenized in Hepes-sucrose buffer (pH 7.4) with a Teflon-glass homogenizer and centrifuged at 1000 × g for 10 minutes. The pellets are suspended in ice-cold Tris-HCl buffer (pH 7.7) with 5mM ethylene diamine tetracetic acid and homogenized using a Polytron (Brinkman Instruments) for 10 seconds. The homogenate is centrifuged at 40,000 × g for 30 minutes to produce a membrane pellet. The membrane pellet is washed three times by resuspending in buffer and re-centrifuging. The washed pellet is suspended in fresh Tris-HCl buffer (pH 7.4) to provide approximately 100 µg protein per assay tube. Binding assays are performed in Tris-HCl buffer (pH 7.7) using 5 nM of tritiated test compound. Non-specific binding is defined by 100 µM of unlabelled idazoxan which will inhibit the specific binding of $^3$H-idazoxan. Thus the binding remaining in the presence 100 µM of idazoxan is due to non-specific binding and this will be substracted from total binding to calculate the specific binding. Following incubation at 25° C. for 30 minutes, reaction is terminated by rapid vacuum filtration over Whatman GF/B filters and washed with 10 ml of ice-cold buffer. Filters are suspended in scintillation fluid and radioactivity counted in a liquid scintillation counter. Membrane protein is assayed by Coomassie Blue method (Pierce) using bovine serum albumin as standard.

Determination of inhibition constant ($K_i$) for each drug is determined as follows: The binding of $^3$H-idazoxan to membranes of vascular smooth muscle cells is determined in the presence of 0.1 nM to 100 µM concentrations of potential drug. The percent inhibition of specific binding of $^3$H-idazoxan by each concentration is calculated and plotted against concentration. The data is analyzed by non-linear curve fitting program, LIGAND and the $IC_{50}$ value for each potential drug is calculated. The affinity for each drug ($K_i$) for $I_2$ imidazoline receptors is calculated using the formula $K_i = IC_{50}/1 + L/K_d$ where L is the concentration of $^3$H-idazoxan used for binding and $K_d$ is the dissociation constant for $^3$H-idazoxan for $I_2$ imidazoline receptors. The dissociation constant ($K_d$) is determined by Scatchard analysis of the saturation binding of $^3$H-idazoxan using the formula $$\frac{B}{F} = \frac{B_{max} - B}{K_d}$$

where B and F are the amount of bound and free ligand, respectively, and $B_{max}$ is the number of binding sites. Drugs that exhibit an affinity of less than 500 nM are tested for their antiproliferative action as described below.

Inhibition of serum-stimulated proliferation of rat aortic smooth muscle cells is determined as follows: The antiproliferative effect of potential drug is determined by measuring the incorporation of $^3$H-thymidine into cellular DNA. Exposure of quiescent vascular smooth muscle cell to serum, which contains many growth factors, results in a large increase in cellular proliferation as measured by $^3$H-thymidine incorported into DNA. The inhibitory effect of potential drug on serum-stimulated proliferation is tested by adding a drug before the addition of serum and determining if the serum-stimulated proliferation is reduced. If a drug that binds with high affinity to $I_2$ imidazoline receptors does not exhibit antiproliferative effect, the reason may be that it is an antagonist at this receptor. In that event, antagonizing of the antiproliferative effect of idazoxan is determined by adding antagonist before the addition of idazoxan to serum-stimulated vascular smooth muscle cells. Such antagonists at 12 imidazoline receptors reverse the antiproliferative effect of idazoxan.

The term "vascular smooth muscle cell antiproliferative effective amount" is used herein to mean an amount which causes reduction or elimination in the proliferation of vascular smooth muscle cells that would occur Without the administration of the $I_2$ imidazoline receptor agonist.

DETAILED DESCRIPTION

The patients in need of inhibiting the proliferation of vascular smooth muscle cells include those afflicted with atherosclerosis, those at risk for or having blockage of artery after coronary angioplasty (restenosis) or traumatic injury to blood vessels including that resulting from surgical grafts or insertion of balloon catheters or stents, and those afflicted with diabetic retinopathy, and those afflicted with other disorders in which vascular proliferation is prominent including fibrovascular displacia of the renal artery and arteritides of various etiologies, e.g., collagen vascular disorder.

The structure, description and source of illustrative $I_2$ imidazoline receptor agonists are listed below in Table 1.

TABLE 1

| DRUG | SOURCE | FORMULA | REFERENCE |
| --- | --- | --- | --- |
| Idazoxan | Research Biochemical Int. (RBI) (Natick, MA) | 2-[2-(1,4-benzodioxanyl)]-2-imidazoline | British Patent application 2,068,376 - August, 1981 |
| UK 14,304 | RBI | 5-bromo-N-(4,5-dihydro-1-H-imidazol-2-yl)-6-quinoxalinamine | Paris et al., Mol. Pharmacol. 35:345–354, 1989 |
| Naphazoline | RBI | 2-(1-naphthylmethyl) imidazoline | Merck Index, 11th Edition, p. 1008, No. 6287 |
| Cirazoline | RBI | cyclopropyl phenoxy imidazoline | Wikberg et al., J. Neurochem. 55:192–203, 1990 |
| BFI | Tocris-Cookson (St. Louis, MO) | benzofuranyl-2-imidazoline | Nutt et al., Ann. NY Acad. Sci. 763:125–139, 1995 |
| BU239 | Tocris-Cookson | 2-(4,5-dihydroimidaz-2-yl)-quinoxaline | Nutt et al., Ann. NY Acad. Sci. 763:125–139, 1995 |
| Efaroxan | RBI | 2-(2-ethyl-2,3-dihydro-2-benzofuranyl)-4,5-dihydro-1H-imidazole | Langin et al., Eur. J. Pharmacol. 159:199–205, 1989 |
| Antazoline | Tocris-Cookson | [4,5-dihydro-N-phenyl-N-(phenylmethyl)]-1H-imidazole-2-methanamine | Berden et al., Eur. J. Pharmacol. 275:91–98, 1995 |
| Atipimazole | Orion-Farmos (Turku, Finland) | 4-(2-ethyl-2,3-dihydro-1H-inden-2-yl)-1H-imidazole | Sjoholm et al., Ann. NY Acad. Sci. 763:66–77, 1995 |
| Detomedine | Orion-Farmos | 4-(2,3-dimethyl phenyl) ethyl imidazole | Rangel et al., Pharmacol. Toxicol. 73:86–90, 1993 |
| LSL 60101 | Lasa Laboratories (Barcelona, Spain) | 2-(2-benzofuranyl) imidazole | Alemany et al., Eur. J. Pharmacol. 280:205–210, 1995 |
| Agmatine | RBI | 4-(aminobutyl guanidine) | Merck Index, 11th Edition, p. 31, No. 176 |

The $I_2$ imidazoline receptor agonists preferably do not include agmatine or any diamine or polyamine. In other words, a preferred class of $I_2$ imidazoline receptor agonists excludes agmatine or any diamine or polyamine.

All presently known agonists at $I_2$ imidazoline receptors also bind to $\alpha_2$-adrenergic receptors and act either as agonists (e.g. UK 14034) or antagonists (e.g.idazoxan). Since $\alpha_2$-adrenergic agonists may exhibit undesirable side-effects particularly hypotension and drowsiness, a selective $\alpha_2$-adrenergic antagonist, that is an $\alpha_2$-adrenergic antagonist which does not bind to $I_2$ imidazoline receptor (e.g. rauwolscine or yohimbine) can be co-administered to prevent these side-effects. However, it is desirable that $I_2$ imidazoline receptor agonists for use herein be $\alpha_2$-adrenergic antagonists or preferably be devoid of any activity at $\alpha_2$-adrenergic receptors.

In general, the dosage for the $I_2$ imidazoline receptor agonist treating agents herein ranges from 50 to 1,200 mg/day and administration is carried out for as many days as needed to stabilize the condition treated and for as long as benefit is obtained or in the case of those undergoing angioplasty or stent insertion for as long as is necessary to minimize the occurrence of vascular smooth muscle cell proliferation. For those undergoing angioplasty or stent insertion, treatment may be started up to 10 days before angioplasty and preferably is continued for up to 30 days or more after angioplasty. In the other cases, treatment preferably commences as soon as practical after diagnosis.

The dosage for idazoxan preferably ranges from 50 to 100 mg/day regardless of the condition being treated. The dosage for UK 14,304, naphazoline, BFI, and BU 239 preferably ranges from 100 to 150 mg/day regardless of the condition being treated. The dosage for efaroxan, antazoline, atipimazole, detomedine and LS 60101 preferably ranges from 500 to 700 mg/day regardless of the condition being treated. The dosage for cirazoline preferably ranges from 50 to 75 mg/day regardless of condition being treated. The dosage for agmatine preferably ranges from 800–1000 mg/day regardless of the condition being treated.

Administration of the $I_2$ imidazoline receptor agonist is preferably carried out orally but also may be carried out by other routes of administration, e.g., locally, subcutaneously, or parenterally. For the oral administration, the $I_2$ imidazoline receptor agonist is preferably administered in association with a pharmaceutically acceptable carrier, for example, an inert diluent such as sodium carbonate, lactose or talc. For treating proliferative diabetic retinopathy, the $I_2$ imidazoline receptor agonists are also preferably administered as ophthalmic compositions, e.g., in sodium phosphate solution as drops or as an ointment at a concentration ranging from 0.01% to 2%. For local administration the agent can be administered in proximity to balloon catheters during angioplastic procedures. If local administration is not possible for an angioplastic or stent procedure, administration by an intravenous route is appropriate.

The following in vitro examples are included to show that the invention is operative in vivo.

IN VITRO EXAMPLE 1

Showing that Rat Aortic Smooth Muscle Cells Express Imidazoline Receptors of the $I_2$ Subclass Primary cultures of rat-aortic smooth muscle cells were prepared by a modification (described in Erlinge, Do, et al, Am. J. Physiol. 265, H1089–1097, 1993) of the method of Meyer-Lehnert and Schrier (Meyer-Lehnert, H., et al, Hypertension 13,350–361, 1989), the disclosure of these cited articles being incorporated herein by reference. Briefly, rats were killed by anesthetic overdose and the aorta were removed and incubated with collagenase (2 mg/ml) in Dulbecco's modified Eagle's minimum essential medium (DMEM). The vessel was stripped of adventitia, cut longitudinally and the intima scraped away. After further collagenase treatment, the remaining tissue was passed 20 times through 18 and 16 gauge needles. The resulting cell suspension was centrifuged at 500 × g for 5 minutes and resuspended in DMEM containing penicillin (100 units/ml), streptomycin (100 μg/ml), 2 mM L-glutamine and 10% fetal calf serum. The suspended cells were plated in T-75 flasks, cultured until confluent, and subcultured in 100 mm plates. The confluent cells were harvested and membranes were prepared. Cell viability was determined by trypan blue exclusion. Smooth muscle cells were phenotypically defined by immunostaining with anti-smooth muscle actin (Sigma). The cultured cells were usually used for only about 10 passages after which they were replaced by freshly prepared cells.

Membranes were prepared from the cultured cells as described in Regunathan et al, Biochem. Pharmacol. 45, 1667–1675 (1993). Membranes were incubated with 5 nM of $^3$H-idazoxan, $^3$H-PAC or $^3$H-rauwolscine with non-specific binding defined by 100 μM cold ligand as described above. The specific binding of all three ligands was greater than 70%. Epinephrine (10 μM) completely inhibited specific binding of $^3$H-rauwolscine and $^3$H-PAC but failed to reduce $^3$H-idazoxan binding by greater than 10% even at 100 μM. $^3$H-idazoxan binding (5 nM) was inhibited by idazoxan ($K_i$ of about 10 nM). This indicates that $^3$H-idazoxan binds almost exclusively to non-adrenergic sites in contrast to $^3$H-PAC and $^3$H-rauwolscine which primarily bind to $\alpha_2$-adrenergic receptors.

The specific binding of $^3$H-idazoxan to smooth muscle cell membranes (performed in the presence of 10 μM epinephrine to mask residual binding to $\alpha_2$-adrenergic receptors) was saturable and of high affinity. Scatchard analysis was consistent with a single-site fit with a $K_d$ of 8.9 ±1.2 nM. This is comparable to the kinetics of high affinity binding sites for $^3$H-idazoxan to non-adrenergic sites in other tissues (See Wikberg, J.E.S., et al, J. Neurochem. 55:192–203, 1990). The number of non-adrenergic binding sites ($B_{max}$) was 610 ±45 fmol/mg protein, about 10 fold higher than $\alpha_2$-adrenergic sites measured by $^3$H-rauwolscine.

The pharmacological selectivity of the binding site was analyzed by comparing the potencies of different drugs to inhibit $^3$H-idazoxan (5 nM) binding. The inhibition constants ($K_i$) and pseudo-Hill coefficients ($n_H$) are listed in Table 2 below wherein ND means not determined and values are from two or three different membrane preparations each done in triplicate.

TABLE 2

| | Ki | | Hill Coefficient ($n_H$) |
|---|---|---|---|
| Idazoxan | 8.5 ± 0.35 | nM | 0.95 ± 0.05 |
| Cirazoline | 9.5 ± 0.73 | nM | 0.61 ± 0.03 |
| UK 14,304 | 20 ± 1.4 | nM | 0.69 ± 0.04 |
| Naphazoline | 45 ± 3.8 | nM | 0.58 ± 0.04 |
| Agmatine | 240 ± 25 | nM | 0.63 |
| Tolazoline | 256 ± 23 | nM | 0.89 ± 0.08 |
| Clonidine | 2.5 ± 0.65 | μM | 0.65 ± 0.05 |
| Phentolamine | 10.5 ± 1.4 | μM | 0.75 ± 0.11 |
| Guanabenz | 51 ± 6.5 | μM | ND |
| Amiloride | 75 ± 9.6 | μM | ND |
| Moxonidine | 55 ± 4 | μM | ND |
| Rilmenidine | 85 ± 9 | μM | ND |
| Rauwolscine | >100 | μM | ND |

The selective $\alpha_2$-adrenergic antagonist rauwolscine was without effect.

The affinities of the guanidiniums guanabenz and amiloride and moxonidine and rilmenidine, drugs relatively selective for $I_1$ imidazoline receptors, were low.

The findings indicate that aortic smooth muscle cells express imidazoline receptors of the $I_2$ subclass.

IN VITRO EXAMPLE 2

In vitro showing of Anti-Proliferative Actions of $I_2$ Imidazoline Receptor Agonists In this experiment, the proliferation of vascular smooth muscle cells was determined by measuring DNA replication. The incorporation of $^3$H-thymidine into DNA was used to measure the replication of DNA as described in Erlinge, D., et al, Am. J. Physiol. 265, H1089–H1097 (1993) which is incorporated herein by reference.

Rat aortic smooth muscle cells prepared as described in In Vitro Example 1 were plated into 24-well plates at a density of about 30,000 cells/well in 10% fetal calf serum (FCS). After 48 hours, the cells were starved in 0.5% FCS for another 48 hours to decrease proliferation and induce quiescence. The medium was replaced by serum-free medium 24 hours prior to addition of drug (drugs are described below) and 10% fetal calf serum or only 10% fetal calf serum in the case of the control. The cells were then incubated for 24 hours and $^3$H-thymidine (1 µCi/well) was added at hour 20. At the end of the 24 hour period, the medium was aspirated and the cells were washed three times with phosphate-buffered saline and twice with ice-cold trichloroacetic acid. Fixed cells were then solubilized in 0.2M NaOH and sonicated. A 100 µl aliquot was used for scintillation counting.

In some experiments, the number of cells was measured by counting Trypsin blue-negative cells in a hemocytometer.

To assess cytotoxicity, cells were stained with neutral red following exposure to test compounds and the percent of positive cells was determined.

The results are set forth in Table 3 below wherein the $IC_{50}$ is the concentration of drug inhibiting incorporation of 50% of $^3$H-thymidine into DNA and "N" stands for no effect.

TABLE 3

|  | $_3$H-thymidine Incorporated ($IC_{50}$) | |
|---|---|---|
| Idazoxan | 4.5 ± 1.4 | µM |
| UK 14,304 | 15.6 ± 2.8 | µM |
| Naphazoline | 52.3 ± 5.6 | µM |
| Cirazoline | 285.8 ± 19 | µM |
| Agmatine | 340 ± 29 | µM |
| Rilmenidine | N | |
| Moxonidine | N | |
| Tolazoline | N | |
| Rauwolscine | N | |
| Clonidine | N | |
| Phentolamine | N | |

As indicated in Table 3, in respect to drugs shown to bind with high affinity ($K_i$ values in Table 2), idazoxan, UK 14,304, and naphazoline potently inhibited vascular smooth muscle cell proliferation and cirazoline and agmatine weakly inhibited the proliferation and tolazoline was without any effect. Clonidine, rilmenidine and moxonidine, drugs relatively selective for imidazoline receptors of the $I_1$ subclass, had no effect. Rauwolscine, a selective $\alpha_2$-adrenergic receptor antagonist, had no effect.

The fact that tolazoline failed to inhibit cellular proliferation even though binding with high affinity to $I_2$ imidazoline receptors (see Table 2) raised the possibility that tolazoline may be an $I_2$ imidazoline receptor antagonist. To test this, the effect of tolazoline (100 µM) on the concentration/response curve was determined. It markedly shifted the concentration/response curve for idazoxan to the right and increased the $IC_{50}$ for idazoxan to 55 µM from 4.5 µM. These results indicate that tolazoline is an $I_2$ imidazoline receptor antagonist.

The results were confirmed by number of cells (determined by counting) and amount of protein content in cultured vascular smooth muscle cells stimulated by 10% fetal calf serum. Since viability of cells exposed to each agent remained greater than 95%, the responses cannot be attributed to cytotoxicity.

The affinity for imidazoline receptors and inhibitory response correlated after determination that tolazoline is a $I_2$ imidazoline receptor antagonist.

The anti-proliferative responses cannot be attributed to interactions with $\alpha_2$-adrenergic receptors since the effect was blocked by rauwolscine, a highly selective $\alpha_2$-adrenergic receptor antagonist and occurred irrespective of whether the agent was an agonist (UK 14,304 and naphazoline) or antagonist (idazoxan) at $\alpha_2$-adrenergic site. The findings support the observations of others that stimulation of $\alpha_2$-adrenergic receptors may slightly increase but does not inhibit the proliferation of vascular smooth muscle cells (Nakaki, T., et al, Mol. Pharmacol. 37, 30–36, 1990; Jackson, C. L., et al, Hypertension 20, 713–735, 1992).

The results indicate that the anti-proliferative actions of idazoxan and other agents result from stimulation of imidazoline receptors of the $I_2$ subclass and not from activation of $\alpha_2$-adrenergic receptors. The persistence of binding in the presence of saturating concentrations of epinephrine (In Vitro Example 1) indicates binding to non-adrenergic binding sites.

The invention is illustrated by the following examples.

IN VITRO EXAMPLE 3

Antiproliferative Actions of Idazoxan in Human Coronary Artery Smooth Muscle Cells In this experiment the antiproliferative action of idazoxan was tested in normal human coronary artery smooth muscle cells (Clonetics Corp.). Proliferation of smooth muscle cells was measured as described above by the incorporation of $^3$H-thymidine into cellular DNA. Following the incubation of semi-confluent smooth muscle cells in serum-free medium for 24 hr, growth is stimulated by either 5% fetal calf serum (FCS) or platelet derived growth factor (PDGF) (10 ng/well) in the presence and absence of various concentrations of idazoxan. As shown in Table 4 below, idazoxan inhibited the incorporation of $^3$H-thymidine into smooth muscle cells stimulated by fetal calf serum (FCS) or platelet-derived growth factor (PDGF). These results confirm that actions of $I_2$ imidazoline receptor agonists in inhibiting proliferation of rat vascular smooth muscle cells are also true for human vascular smooth muscle cells. In Table 4, "DPM" stands for disintegrations per minute which is a measure of the radioactivity incorporated into the cellular DNA by 3H-thymidine.

TABLE 4

|  | $^3$H-thymidine Incorporated (DPM/well) |
|---|---|
| Control (no serum) | 554 ± 87 |
| FCS (5%) | 6550 ± 450 |
| PDGF (10 ng/well) | 4450 ± 345 |
| FCS + idazoxan (1 µM) | 5540 ± 430 |
| FCS + idazoxan (10 µM) | 2370 ± 230 |
| FCS + idazoxan (100 µM) | 430 ± 98 |
| PDGF + idazoxan (1 µM) | 3220 ± 180 |
| PDGF + idazoxan (10 µM) | 1890 ± 210 |
| PDGF + idazoxan (100 µM) | 340 ± 60 |

The invention is illustrated by the following in vivo examples.

Example I

A 65 year old male presents with progressive symptoms of intermittent claudication in both legs. Angiography reveals narrowing and near occlusion of both iliac arteries with atheromatous plaques. Oral administration of 50 and 75 mg/day of idazoxan for over 30 days results in stabilization of symptoms as does substitution for the idazoxan of UK 14,304 at a dose of 125 mg/day, naphazoline at a dose of 125 mg/day, cirazoline at a dose of 75 mg/day or agmatine at a dose of 900 mg/day.

Example II

A 72 year old female presents with a history of intermittent brief episodes of transient monocular blindness in the right eye associated with clumsiness and weakness of the left arm and leg. Angiography indicates substantial narrowing of the right common carotid artery. She is with treated with idazoxan at a dosage of 50 or 75 mg/day for two weeks preceding balloon angiography and for 3 months thereafter. Symptoms disappear without evidence of restenosis of the vessel. Substitution for the idazoxan of UK 14,304 at a dose of 125 mg/day, cirazoline at a dose of 60 mg/day, naphazoline at a dose of 125 mg/day or agmatine at a dose of 900 mg/day will have comparable results.

Example III

A 72 year old male presents with the onset of chest pain on exertion. Stress testing suggests coronary artery disease which is substantiated when cardiac catheterization and angiography reveals disease localized to left anterior descending artery. Ten days before angioplasty, the patient is begun on 75 or 100 mg/day of idazoxan. Angioplasty is carried out with improved coronary blood flow. The patient has no further chest pain. Treatment with 50 mg/day idazoxan is continued for 3 months. The patient remains symptomless without evidence of restenosis. Substitution for the idazoxan of UK 14,304, naphazoline, cirazoline or agmatine will have comparable results, i.e., no restenosis.

Example IV

A 25 year old man presents with a history of headaches and shortness of breath. Upon examination he has a blood pressure of 180/124 with an elevated in plasma renin profile and positive captopril test. Angiography reveals that the lumen of the right renal artery is narrowed by over 75% without evidence of atherosclerosis elsewhere. A diagnosis of fibromuscular dysplasia of the renal artery is made. Treatment with idazoxan (75 mg/day) for 1 month followed by angioplasty with continued treatment results in a rapid fall of blood pressure to normal without evidence months later on re-elevation of pressure or on follow up, of restenosis of the renal artery. Substitution for the idazoxan of UK 14,304 at a dose of 60 mg/day, naphazoline at a dose of 125 mg/day, cirazoline at a dose of 60 mg/day or agmatine at a dose of 900 mg/day will have comparable results, i.e., no restenosis.

Example V

A 32 year old female with Type I diabetes mellitus and maintained on insulin presents with progressive symptoms of loss of visual acuity bilaterally with evidence on opthalmascopic examination of overgrowth of retinal vessels and hemorrhages. Treatment with idazoxan (75 mg/day) is begun with arrest of the progression and some regression of the visual symptoms. Substitution for the idazoxan of UK 14,304 at a dose of 60 mg/day, naphazoline at a dose of 125 mg/day, cirazoline at a dose of 60 mg/day or agmatine at a dose of 900 mg/day will have comparable results, i.e., no restenosis.

EXAMPLE VI

Antiproliferative effect of idazoxan in rat carotid artery:

To determine the actions of idazoxan in inhibiting the proliferation of vascular smooth muscle cells in vivo, we tested the effect of balloon angioplasty in rat carotid artery. Left common carotid artery balloon angioplasty was performed as described by Ohlstein et al, Proc. Natl. Acad. Sci. 90, 6189–6193 (1993). Rats were implanted, subcutaneously, with Alzet minipumps (1 μl/hr delivery rate) containing idazoxan to deliver a dose of 10 mg/kg/24hr for 7 days. Control rats were implanted with minipumps containing sterile saline. Ballon angioplasty of left common carotid artery was performed on fourth day of idazoxan administration and animals were sacrificed 10 days after the surgery. Left and right common carotid arteries were removed, cross-sections (10 μm) were cut in a cryostat and stained with eosin and hematoxylin. Blood vessel layers were quantitated in an imaging system and the ratio of internal and external diameters were calculated. There was no significant difference in the ratio between the control and idazoxan treated animals in the non-injured right common carotid artery indicating that idazoxan treatment did not affect normal arteries. When the ratio of lesion side was calculated as percent of control side, there was significant decrease in the percent after idazoxan infusion (21.9 ±3.3 saline control vs 6.5 ±3.4 idazoxan treatment) following ballon angioplasty of left common carotid artery. Thus, idazoxan inhibited the proliferation of smooth muscle cells in vivo in ballon injury model of arterial thickening.

Variations of the invention will be obvious to those skilled in the art. Therefore, the invention is defined by the claims.

What is claimed is:

1. A method of inhibiting the proliferation of vascular smooth muscle cells in a patient in need of such inhibiting, comprising administering to the patient a vascular smooth muscle cell antiproliferative effective amount of an $I_2$-imidazoline receptor agonist.

2. The method of claim 1 wherein the patient is afflicted with atherosclerosis.

3. The method of claim 1 wherein the patient is at risk for or having blockage of artery after coronary angioplasty or angioplasty or vascular surgery of other arteries to correct narrowing.

4. The method of claim 1 wherein the patient has sustained injury to blood vessel from trauma or by vascular grafts or insertion of stents.

5. The method of claim 1 wherein the patient is afflicted with proliferative diabetic retinopathy.

6. The method of claim 1 wherein the patient has suffered from progressive arteritis related to collagen vascular disorder.

7. The method of claim 1 wherein the $I_2$ imidazoline receptor agonist is idazoxan.

8. The method of claim 1 wherein the $I_2$ imidazoline receptor agonist is not agmatine or any diamine or polyamine.

* * * * *